May 28, 1935. R. ROBERTSON Plant Pat. 126
ORANGE TREE
Filed Feb. 5, 1935
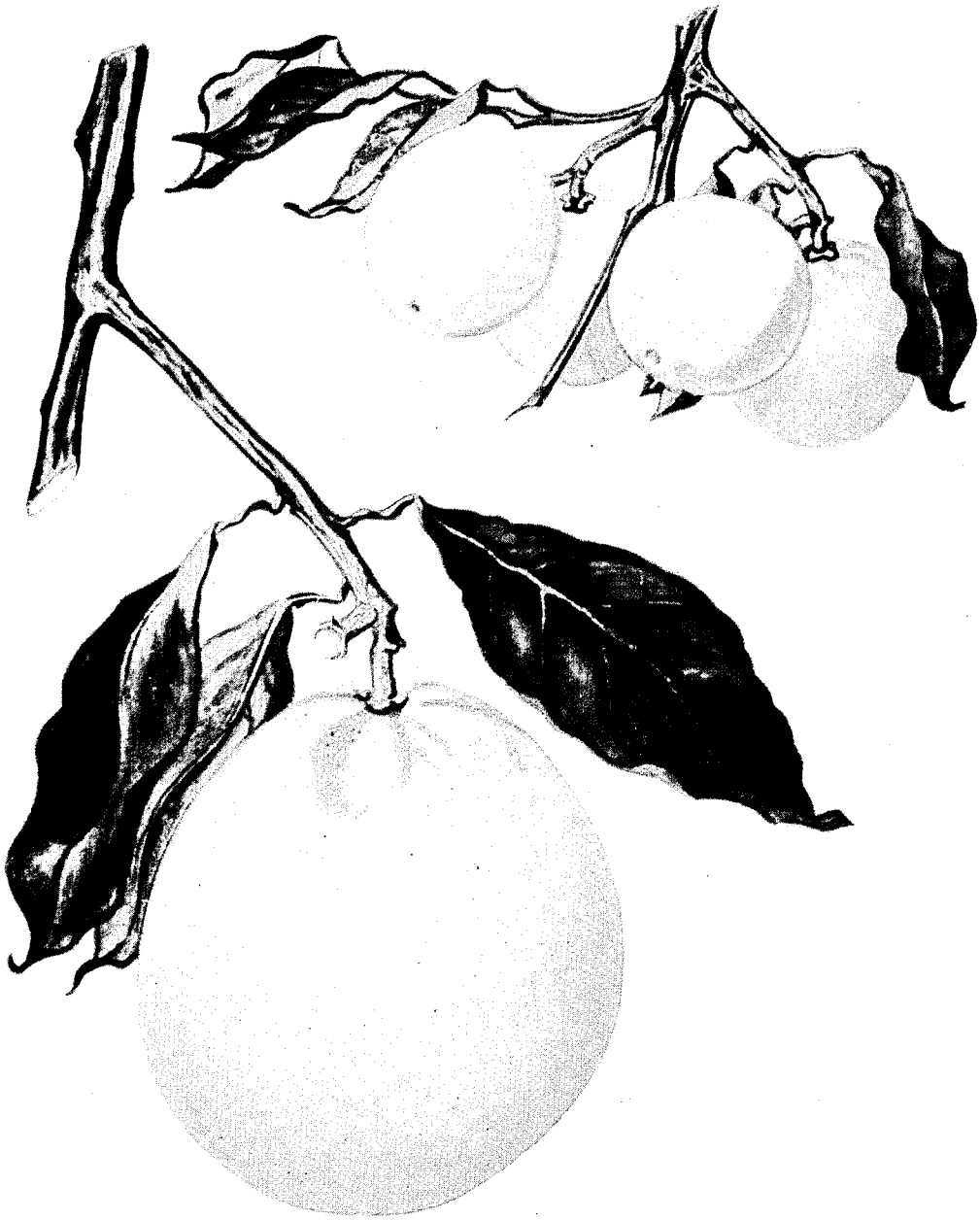
INVENTOR
Roy Robertson
By Orville M Kile
PLANT PATENT AGENT Patented May 28, 1935 Plant Pat. 126

UNITED STATES PATENT OFFICE

126

ORANGE TREE

Roy Robertson, Redlands, Calif., assignor to Armstrong Nurseries, Ontario, Calif.

Application February 5, 1935, Serial No. 5,081

1 Claim. (Cl. 47—62)

My new variety of orange tree is an improvement in the class of oranges known as navel oranges largely grown for commercial purposes. I first observed this new variety in the spring of 1925, in an orange grove near Redlands, California. It occurred as a single limb sport on an ordinary Washington navel orange tree. I continued to observe this limb throughout a period of two years and assisted in taking budwood and topworking same on another orange tree for experimental purposes and further observation. Later a considerable number of reproductions were made both by topworking and by budding young seedlings. These have now borne fruit. By these various means it has been definitely established that this is not only a new and desirable variety but that it reproduces readily and true to type.

The accompanying illustration shows in full color and approximately natural size a single typical fruit and stem with foliage. There is also shown a diagrammatic representation of a typical cluster arrangement characteristic of this new variety of navel orange tree.

A more detailed description follows.

In general the tree, foliage and fruit closely resemble the well known Washington navel variety in size, shape, color, and texture and quality of rind and flesh of the fruits. Since detailed descriptions of the Washington navel orange are common and readily available, this new variety can be best described by comparing it with the Washington navel orange and indicating the principal points of difference between the two varieties.

*The tree.*—Has a somewhat more pendant or drooping appearance than the Washington variety, due in part to the extra heavy crops of fruit which tend to pull the branches downward. Very little sucker or non-fruit-bearing growth is found in the average tree of this new variety, so that practically all the branches are pulled down by the weight of the fruit.

The size, shape and color of the leaves are apparently the same as found in the Washington variety.

*Blossoming and fruiting habits.*—This variety blossoms at practically the same time as the ordinary Washington variety but the young fruits of the new variety grow much more rapidly and by so doing they become large and strong enough to resist the usual heavy "June drop".

Tests made in southern California in 1933, on samples of typical fruits of this new variety and of the Washington variety, showed that on May 29 those of the new variety were much larger than those of the Washington variety; on June 15 the former were approximately four times larger than the latter; on July 13 typical fruits of the new variety measured 5.4 inches in circumference, while those of the Washington variety measured only 4.1 inches. The greatest difference in size occurs in June and then the difference gradually disappears until at harvest time in November and December the two varieties are about the same size. On especially heavily laden trees at harvest the fruits of the new variety may be slightly smaller than those of the Washington variety.

The fruits of this new variety tend to grow in clusters of three to five and occasionally eight to ten fruits in a single compact group. This fact, together with the escaping of the June drop above referred to, results in the production of heavy crops every year. During all the years in which this new variety has been observed it has never failed to bear abundant crops of fruit. There are appparently no "off years".

*Ripening.*—This new variety ripens its fruit two to three weeks earlier than the Washington variety when grown under normal comparable conditions. This is not merely a surface color indication but is shown also by tests of the soluble solids and acids ratio.

On December 1, 1933, examination of typical fruits of this new variety in southern California showed that the yellowish-orange color had developed to a point where the fruits would easily pass the California maturity color standards while on the same date the Washington navel fruits were so green as to fall considerably below the standard requirements and were at least three weeks later in this respect.

*Texture of rinds.*—Is somewhat smoother than that of the Washington navel variety. Thickness and color are about the same in both varieties.

*Quality of fruit.*—The color, amount of rag and the tenderness of the flesh, and the amount and flavor of the juice are practically the same as in the Washington variety.

*Size of navels.*—Some of the youngest trees, particularly those that have made the most vigorous vegetative growth, sometimes produce fruits having somewhat protruding navels and with large openings. In those trees that have been in bearing for several years and in which vegetative growth is moderate, only about the same number of large navels are found as occur in the Washington variety. The typical fruit is remarkably smooth at the navel end and has but a very small opening.

Having thus disclosed my invention, I claim;

The variety of navel orange tree herein described and illustrated, characterized particularly by its heavier and more uniform production of fruits of the Washington navel variety type, but occurring in clusters and maturing two to three weeks earlier.

ROY ROBERSTON.